(12) United States Patent
Hamrani et al.

(10) Patent No.: US 12,367,581 B1
(45) Date of Patent: Jul. 22, 2025

(54) SYSTEMS AND METHODS FOR SKIN COLOR CLASSIFICATION

(71) Applicants: Abderrachid Hamrani, Miami, FL (US); Anuradha Godavarty, Miami, FL (US)

(72) Inventors: Abderrachid Hamrani, Miami, FL (US); Anuradha Godavarty, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 18/943,415

(22) Filed: Nov. 11, 2024

(51) Int. Cl.
  *G06T 7/00* (2017.01)
  *A61B 5/00* (2006.01)

(52) U.S. Cl.
  CPC .......... *G06T 7/0012* (2013.01); *A61B 5/0059* (2013.01); *A61B 5/445* (2013.01); *A61B 5/742* (2013.01); *G06T 2207/10004* (2013.01); *G06T 2207/20016* (2013.01); *G06T 2207/20048* (2013.01); *G06T 2207/20076* (2013.01); *G06T 2207/20081* (2013.01); *G06T 2207/30088* (2013.01)

(58) Field of Classification Search
  CPC ..... A61B 5/441; A61B 5/0077; A61B 5/1032; A61B 2576/00; A61B 2576/02; A61B 5/445; A61B 5/4842; A61B 5/4848; A61B 5/7275; A61B 5/0064; A61B 5/444; A61B 5/0082; A61B 5/0059; A61B 5/742; G06T 2207/30088; G06T 7/0012; G06T 7/0016; G06T 2207/10004; G06T 2207/20016; G06T 2207/20048; G06T 2207/20076; G06T 2207/20081; G16H 30/40; G16H 50/30; G16H 50/20
  See application file for complete search history.

(56) References Cited

U.S. PATENT DOCUMENTS

| | | | |
|---|---|---|---|
| 6,215,893 B1 * | 4/2001 | Leshem | A61B 5/444 382/128 |
| 11,350,826 B2 * | 6/2022 | Secco | A61B 5/746 |
| 2010/0121201 A1 * | 5/2010 | Papaioannou | A61B 5/0064 382/128 |
| 2010/0185064 A1 * | 7/2010 | Bandic | A61B 5/444 600/306 |

(Continued)

OTHER PUBLICATIONS

N. Mehmood, S. J. Khan and M. Rashid, "K-means Clustering-based Color Segmentation on Vitiligo Skin Lesion," 2022 International Conference on Emerging Trends in Smart Technologies (ICETST), Karachi, Pakistan, 2022, pp. 1-5, doi: 10.1109/ICETST55735. 2022.9922940. (Year: 2022)*

(Continued)

*Primary Examiner* — Aaron W Carter
*Assistant Examiner* — Courtney Joan Nelson
(74) *Attorney, Agent, or Firm* — SALIWANCHIK, LLOYD & EISENSCHENK

(57) ABSTRACT

Systems and methods for classification and/or analysis of skin color(s) are provided. The technology integrates artificial intelligence (AI) with dermatology to enhance skin color classification. The unique matching technique aligns skin images with the Fitzpatrick skin type palette through Euclidean distance matching, achieving higher precision in skin color classification compared to conventional methods.

20 Claims, 13 Drawing Sheets

(56) References Cited

U.S. PATENT DOCUMENTS

2017/0076446 A1* 3/2017 Pedersen ............... G06T 7/194
2018/0279943 A1* 10/2018 Budman ............. A61B 5/0077

OTHER PUBLICATIONS

Adelekun, Ademide et al. "Skin color in dermatology textbooks: an updated evaluation and analysis." Journal of the American Academy of Dermatology 84.1 (2021): 194-196.
Ho, Byron K. et al. "Color bar tool for skin type self-identification: a cross sectional study." Journal of the American Academy of Dermatology 73.2 (2015): 312.
Kaile, Kacie et al. "Machine learning algorithms to classify Fitzpatrick skin types during tissue oxygenation mapping." Optical Tomography and Spectroscopy. Optica Publishing Group, 2022.
Leizaola, Daniela et al. "Deep learning algorithms to classify Fitzpatrick skin types for smartphone-based NIRS imaging device (Erratum)." Next-Generation Spectroscopic Technologies XV. vol. 12516. SPIE, 2024.
Marguier, Joanna et al. "Assessing human skin color from uncalibrated images." International Journal of Imaging Systems and Technology 17.3 (2007): 143-151.
Sobhan, Masrur et al. "Subject skin tone classification with implications in wound imaging using deep learning." 2022 International Conference on Computational Science and Computational Intelligence (CSCI). IEEE, 2022.

* cited by examiner

| Task | Tool description |
|---|---|
| Image processing (OpenCV) | OpenCV (Open-Source Computer Vision Library)(Bradski & Kaehler, 2008) was integral for image processing and computer vision tasks. It facilitated crucial operations such as reading, resizing, and transforming images, as well as converting them between color spaces. These processes were essential for standardizing the dataset and optimizing the images for further analysis in skin color classification. OpenCV's comprehensive functionalities in image manipulation thus played a pivotal role in preprocessing, laying the groundwork for the subsequent machine learning applications within AIDA. |
| Data processing (NumPy/Pandas) | The incorporation of the NumPy and Pandas libraries (Wes McKinney, 2017) was critical in managing and processing data for machine learning applications. NumPy, renowned for its capabilities in numerical computing, was primarily utilized for its efficient array (vector, matrix) operations. These operations are fundamental in handling image data, facilitating the manipulation and computation tasks essential in machine learning algorithms. Concurrently, Pandas, a library specifically designed for data manipulation and analysis, was employed to handle structured data effectively. |
| Machine learning (Scikit-Learn) | The integration of Scikit-Learn and Scikit-Image libraries played a crucial role in both machine learning and image processing aspects. Scikit-Learn (Pedregosa et al., 2011), a prominent machine learning library, was utilized to implement the clustering algorithm. This algorithm was a vital component of the AIDA system, enabling the effective grouping and classification of skin color data. In parallel, Scikit-Image, known for its comprehensive collection of image processing algorithms, was primarily engaged for color space conversions. Functions such as rgb2lab and deltaE_cie76 within Scikit-Image facilitated the conversion of images from RGB to LAB color space and the calculation of color differences. These conversions and calculations were integral to achieving accurate skin color analysis. Additionally, the metrics module from Scikit-Learn provided essential functions like Silhouette_score, Calinski_Harabasz_score, and Davies_Bouldin_score. These functions were indispensable in assessing the performance of the clustering models, providing quantitative measures to evaluate the effectiveness, efficiency, and accuracy of the AIDA system in categorizing skin colors. Together, these libraries formed a comprehensive toolkit, enhancing the AIDA system's capabilities in both machine learning and image processing domains. |
| Plotting and visualization (Seaborn/Matplotlib) | Seaborn and Matplotlib libraries were utilized to facilitate advanced data visualization. Seaborn (Waskom, 2021) offered a high-level interface for creating aesthetically pleasing and informative statistical graphics. This library was instrumental in the project for generating complex plots such as scatter plots and histograms, which played a crucial role in data analysis. Complementing Seaborn, Matplotlib was employed for its robust capabilities in crafting various figures and graphs. This included the production of detailed scatter plots and histograms, which were essential for visualizing the data and the results derived from the AIDA system. The integration of Seaborn and Matplotlib provided a powerful combination for visual representation, allowing for an insightful and clear interpretation of the complex data sets involved in skin color analysis. |

FIG. 12

| Fitzpatrick Scale (FST) | Index of subject samples utilized for CNN Training/Testing | Index of subject samples utilized for comparison analysis of CNN vs. AIDA |
|---|---|---|
| FST - 1 | 17, 29 | 32, 35 |
| FST - 2 | 4, 5, 6, 34 | 36, 38, 39 |
| FST - 3 | 7, 8, 9, 10, 15 | 21, 22, 26, 30, 33, 37 |
| FST - 4 | 1, 2, 3, 12, 16, 18 | 19, 23, 27, 28, 41 |
| FST - 5 | 13, 14, 25, 31, 40 | 42, 43, 44, 45, 48 |
| FST - 6 | 11, 24 | 46, 47 |

FIG. 13

SYSTEMS AND METHODS FOR SKIN COLOR CLASSIFICATION

GOVERNMENT SUPPORT

This invention was made with government support under EB033413 awarded by the National Institutes of Health. The government has certain rights in the invention.

BACKGROUND

Traditional methods for classifying and analyzing human skin colors, such as subjective visual assessments and imagery classification systems, have limitations, especially under variable environmental conditions. In more detail, dermatological research faces a significant challenge in the accurate classification and analysis of skin colors. The vast diversity and complexity of human skin colors call for advanced methods capable of discerning subtle variance. Traditional approaches in skin color classification, predominantly relying on subjective visual assessments, address the skin's reaction to light exposure rather than its actual color, highlighting a critical limitation in comprehensively representing the true spectrum of skin colors.

In an effort to advance beyond these traditional methods, the field has seen the adoption of conventional imaging technologies and digital photography. However, these technologies often inadequately represent the full range of skin colors, especially under variable lighting conditions. Moreover, the emergence of artificial intelligence (AI) systems utilizing convolutional neural networks (CNNs) offers a more objective stance but is hindered by their dependence on extensive labeled datasets, struggling to address the inherent diversity and complexity of skin colors.

BRIEF SUMMARY

Embodiments of the subject invention provide novel and advantageous systems and methods for classification and/or analysis of skin color(s). The technology, which can be referred to herein as Artificial Intelligence Dermatochroma Analytica (AIDA), integrates artificial intelligence (AI) with dermatology to enhance skin color classification. AIDA addresses the limitations of traditional skin color analysis methods, which rely on subjective visual assessments and are challenged by environmental conditions. The unique matching technique of embodiments of the subject invention aligns skin images with the Fitzpatrick skin type (FST) palette through Euclidean distance matching, achieving higher precision in skin color classification compared to conventional methods. AIDA's performance, validated against a supervised convolutional neural network (CNN) model, demonstrates that it is more accurate, efficient, and personalized for dermatological care, showcasing a predictive accuracy rate significantly superior to traditional methods.

In an embodiment, a system for classification of skin color can comprise: a processor; and a (non-transitory) machine-readable medium in operable communication with the processor and having instructions stored thereon that, when executed by the processor, perform the following steps: i) receiving first data of at least one image of skin of a subject (e.g., a human subject); ii) transforming the at least one image of the skin of the subject from an original color space to a standardized color space (e.g., LAB) to produce standardized data; iii) using an unsupervised learning model to perform clustering and matching on the standardized data to give clustered data; and iv) matching cluster centers from the clustered data to cluster centers of an FST to classify each image of the skin of the subject into an FST category/color. The standardized color space can be, for example, LAB color space. The system can further comprise a display in operable communication with the processor and/or the machine-readable medium. The instructions when executed can further perform the following step: v) generating a visualization of colors from the at least one image of the skin of the subject with corresponding respective FST categories/colors; and vi) displaying the visualization on the display. The system can further comprise a ground truth device configured for ground truth classification of the at least one image of the skin of the subject. The instructions when executed can further perform the step of, vii) providing the classification of each image to a clinician to: a) compare to ground truth classifications of each image obtained from the ground truth device; b) use in diagnosis of a medical condition (e.g., diabetes mellitus and/or a diabetic foot ulcer) of the subject; or c) both a) and b). The instructions when executed can optionally further perform the following step: iii-a) before using the unsupervised learning model to perform clustering and matching on the standardized data, training the unsupervised learning model using validated training images of skin color with corresponding FST categories/colors (though, the unsupervised learning model need not be trained and in many embodiments is not trained). The unsupervised learning model can comprise, for example, K-means, K-means-PCA (K-means-principal component analysis), K-means mini-batch, DBSCAN (density-based spatial clustering of applications with noise), HDBSCAN (hierarchical density-based spatial clustering of applications with noise), OPTICS (ordering points to identify the clustering structure), a hierarchical model, a GMM, fuzzy C-means, affinity propagation, mean shift, and/or spectral clustering. For example, the unsupervised learning model can be K-means. The system can further comprise an optical scanner (e.g., a near-infrared (NIR) scanner) to obtain the first data.

In another embodiment, a method for classification of skin color can comprise: i) receiving (e.g., by a processor) first data of at least one image of skin of a subject (e.g., a human subject); ii) transforming (e.g., by the processor) the at least one image of the skin of the subject from an original color space to a standardized color space (e.g., LAB) to produce standardized data; iii) using (e.g., by the processor) an unsupervised learning model to perform clustering and matching on the standardized data to give clustered data; and iv) matching (e.g., by the processor) cluster centers from the clustered data to cluster centers of a Fitzpatrick skin type (FST) to classify each image of the skin of the subject into an FST category/color. The standardized color space can be, for example, LAB color space. The method can further comprise: v) generating a visualization of colors from the at least one image of the skin of the subject with corresponding respective FST categories/colors; and vi) displaying the visualization on a display (e.g., a display in operable communication with the processor). The method can further comprise, vii) providing the classification of each image to a clinician to: a) compare to ground truth classifications of each image obtained from a ground truth device; b) use in diagnosis of a medical condition (e.g., diabetes mellitus and/or a diabetic foot ulcer) of the subject; or c) both a) and b). The method can optionally further comprise: iii-a) before using the unsupervised learning model to perform clustering and matching on the standardized data, training the unsupervised learning model using validated training images of skin color with corresponding FST categories/colors (though, the unsupervised learning model need not be trained and in many embodiments is not trained). The unsupervised learning model can comprise, for example, K-means, K-means-PCA, K-means mini-batch, DBSCAN, HDBSCAN, OPTICS, a hierarchical model, a Gaussian mixture model, fuzzy C-means, affinity propagation, mean shift, or spectral clustering. For example, the unsupervised learning model can be K-means. The first data can be obtained by, for example, an optical scanner (e.g., an NIR scanner).

BRIEF DESCRIPTION OF DRAWINGS

FIG. 7A shows a heatmap, and FIG. 7B shows circular bar charts.

FIG. 11A is for visual classification by a clinician versus visual classification by a researcher both using an FST sticker within image. FIG. 11B is for commercial device FST classification by individual topological angle (ITA) measurement versus visual classification by a researcher using an FST sticker within image. FIG. 11C is for commercial device FST classification by ITA measurement versus visual classification by a clinician using an FST sticker within image.

FIG. 12 shows a table of specific libraries imported and their primary uses

FIG. 13 shows a table of data sets for CNN training and for comparison analysis of AIDA versus CNN.

DETAILED DESCRIPTION

Figure 1:
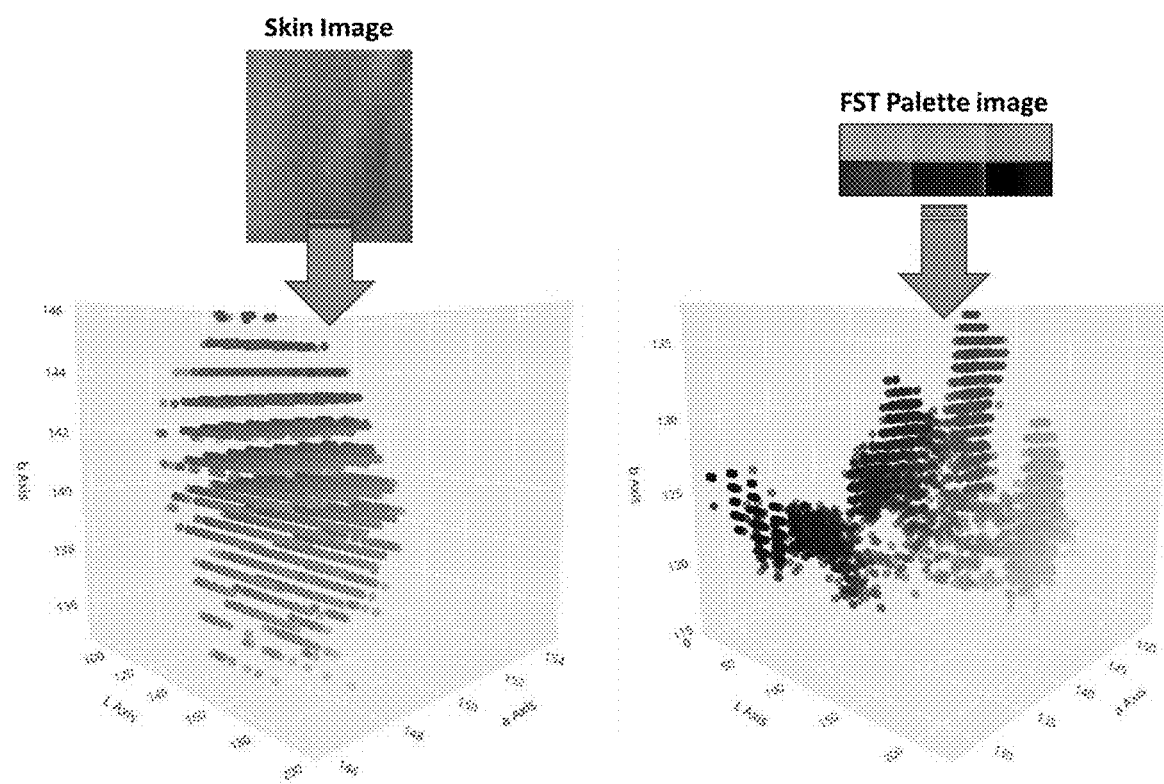
FIG. 1 shows an image transformation to the LAB color space. LAB color space is a color-opponent space with dimension L for lightness and a and b for the color dimensions of redness-greenness and blueness-yellowness, respectively.

Embodiments of the subject invention provide novel and advantageous systems and methods for classification and/or analysis of skin color(s). The technology, which can be referred to herein as Artificial Intelligence Dermatochroma Analytica (AIDA), integrates artificial intelligence (AI) with dermatology to enhance skin color classification. AIDA addresses the limitations of traditional skin color analysis methods, which rely on subjective visual assessments and are challenged by environmental conditions. The unique matching technique of embodiments of the subject invention aligns skin images with the Fitzpatrick skin type (FST) palette through Euclidean distance matching, achieving higher precision in skin color classification compared to conventional methods. AIDA's performance, validated against a supervised convolutional neural network (CNN) model, demonstrates that it is more accurate, efficient, and personalized for dermatological care, showcasing a predictive accuracy rate significantly superior to traditional methods.

AIDA is an advanced AI system designed to revolutionize the classification and analysis of skin color(s) (e.g., human skin color(s)). While related art methodologies struggle to accurately represent the wide spectrum of human skin tones, particularly under varying lighting conditions, AIDA overcomes these challenges by employing state-of-the-art AI technologies, including a variety of unsupervised learning models for image clustering and matching. This enables AIDA to perform as a leading AI clinician in dermatology. The development of AIDA included an exhaustive evaluation of more than 12 distinct unsupervised learning models, such as clustering algorithms (e.g., K-means clustering algorithms), density-based models, hierarchical methods, fuzzy logic approaches, Gaussian techniques, and other advanced methodologies. This rigorous analysis was used to determine the most effective model(s) for AIDA's core clustering operations, which are important for the precise interpretation of skin color variations.

A key feature of AIDA is its integration with the Fitzpatrick six-color scale, a dermatological standard for skin color classification. This ensures that AIDA's analysis is both accurate and relevant to clinical needs. Moreover, AIDA's flexible design allows it to adapt to various skin color scales, making it universally applicable. Also, the methodology behind AIDA encompasses systematic data collection, processing, and evaluation, combined with the integration of sophisticated image clustering and matching algorithms. This comprehensive approach enables AIDA to identify and match skin tones with remarkable accuracy, significantly enhancing its diagnostic capabilities. Comparative analysis (see also Example 3) has shown that AIDA substantially outperforms supervised learning models, such as CNNs, in skin color classification. In particular, AIDA achieved a performance rate nearly double that of CNN models. Additionally, AIDA's predictive accuracy, assessed through a tolerance-based approach, was found to be 97% compared to 87% for CNNs, underlining its superiority in practical clinical scenarios. The combination of advanced clustering techniques and distance matching methodologies underscores AIDA's potential to revolutionize dermatological diagnostics and treatment planning. This marks a significant advancement towards more accurate, efficient, and personalized care in dermatology, showcasing AIDA's innovative approach to addressing the complex challenge of skin color classification and analysis.

In order to address the challenges discussed in the Background section, AIDA is built upon the innovative concept of employing AI for the alignment of segmented skin image clusters with the Fitzpatrick color scale clusters, a technique that surpasses the constraints of conventional methods. Comparing over 12 unsupervised learning models, including clustering algorithms, density-based models, hierarchical methods, probabilistic techniques, fuzzy logic approaches, and other advanced methodologies, AIDA stands out for its unique capability in pattern recognition and data clustering, essential for a nuanced understanding of skin colors.

An important aspect to the framework of AIDA is the Fitzpatrick six-color scale, an established dermatological standard for skin color classification (see also; Fitzpatrick, The Validity and Practicality of Sun-Reactive Skin Types I Through VI, Arch. Dermatol. 124 (1988) 869-871, doi.org/10.1001/ARCHDERM.1988.01670060015008; Alam, Fitzpatrick's Dermatology in General Medicine, 6th ed, Arch. Dermatol. 140 (2004) 372-372, doi.org/10.1001/ARCHDERM. 140.3.372-A; Gupta et al., Skin typing: Fitzpatrick grading and others, Clin. Dermatol. 37 430-436, 2019, doi.org/10.1016/J.CLINDERMATOL.2019.07.010; all three of which are hereby incorporated herein by reference in their entireties). Incorporating this scale into AIDA ensures alignment with dermatological benchmarks while providing a solid basis for the system's performance evaluation. Crucially, the flexibility of AIDA allows for the adaptation to various skin color scales, broadening the scope of its application in diverse dermatological contexts. AIDA has enhanced efficacy over conventional supervised learning models like CNNs, which often reintroduce subjectivity and are labor-intensive due to the need for manual labeling. By leveraging unsupervised learning, AIDA can capitalize on the ability of these algorithms to unravel complex, nonlinear patterns in diverse skin color data, thus overcoming the limitations of related art methods that fail to encompass the entire spectrum of human skin colors. The rigorous development, implementation, and evaluation of AIDA underscore its potential to modernize dermatological diagnostics and treatment planning. Experimental results indicate a significant stride towards more accurate, efficient, and personalized dermatological care, marking the advent of an era where AI-driven personalized care becomes a tangible reality.

Historically, the classification of skin colors largely depended on subjective visual assessment by clinicians. While being straightforward, this suffered from inherent biases and inconsistencies due to individual perception differences. The introduction of the FST classification system marked a significant step forward. Developed in 1975 by Thomas Fitzpatrick, this scale categorizes skin types based on their response to ultraviolet (UV) light, primarily focusing on the tendency to burn or tan. With technological advancements, digital imaging and photography started playing a pivotal role in skin color analysis. These methods provided a more objective data set compared to manual visual assessments, but their effectiveness was often influenced by the variability in camera features and settings, such as exposure and white balance. This variability could significantly impact the perception of skin color. Also, these techniques fall short in fully capturing the diversity of skin colors across different environmental conditions, highlighting a gap in accurately representing the full spectrum of skin tones.

Computerized systems for skin color classification use techniques like colorimetry and spectrophotometry, providing more precise and consistent measurements of skin color. They quantify skin color in standardized color spaces, such as CIELAB, offering a more reliable approach than subjective visual assessments. Though, these methods are still limited by the equipment's sensitivity and the need for controlled environmental conditions. The integration of machine learning (ML), particularly supervised learning models such as CNNs, are a significant advancement in skin color classification. These models bring the promise of learning from large datasets of skin images, offering a more objective and comprehensive analysis. However, their reliance on extensive labeled datasets was a major drawback. The process of labeling, often requiring expert input from dermatologists, is time-consuming and potentially reintroduces subjective biases.

Related art skin color classification methods come with limitations, ranging from subjective biases to technological and practical constraints. AIDA harnesses the power of unsupervised machine learning to overcome these challenges and offer a more accurate, efficient, and inclusive approach to skin color classification. AIDA is an advanced framework designed for the complex task of skin color classification, merging dermatological expertise with advanced machine learning techniques.

AIDA can be structured as an advanced machine learning framework specifically tailored for the analysis and classification of skin colors. At its core, the system can be powered by an unsupervised learning algorithm, selected for its strength in clustering complex, multidimensional data characteristic of skin color(s) (e.g., human skin color(s)). The architecture can be modular, allowing seamless integration and experimentation with different algorithmic approaches. AIDA can be implemented using any suitable programming language (e.g., Python programming language, leveraging its extensive libraries and tools for machine learning applications).

The pseudo-code for the AIDA system is as follows:

Start: Initiate the AIDA system process.

Import Libraries: In the development of AIDA, an important step can include the importation of various libraries essential for machine learning, image processing, and data visualization. These libraries can provide tools and functions to facilitate the implementation of the algorithms and the analysis of the data. A listing of an example of libraries that can be used/imported (along with their primary uses) is shown in the table in FIG. 12.

Load and Preprocess Data: The initial phase of loading and preprocessing skin color and FST palette data can be important for the success of subsequent machine learning tasks. This process can involve importing the image data and converting it into a more analytically suitable format. The images can be transformed from their original color space (i.e., red-green-blue (R-G-B)) to, for example, the LAB color space, as shown in FIG. 1, which is particularly beneficial for skin color analysis due to its ability to provide a nuanced representation of color variations. This standardized approach in data preprocessing can be beneficial to ensure uniformity across the dataset, thus enhancing the accuracy and consistency of the machine learning models used in AIDA.

Configure, cluster, and evaluate clustering model: A methodical approach can be adopted for configuring, clustering, and evaluating the clustering model for image segmentation in the LAB color space. Initially, the parameters of the clustering model, including the number of clusters and the initialization method, can be meticulously configured. The determination of the optimal number of clusters can be guided by the elbow method, a technique that helps identify the point at which the addition of more clusters does not significantly improve the model's performance (see also; Sugar et al., Finding the Number of Clusters in a Dataset, J. Am. Stat. Assoc. 98 (2003) 750-763, doi.org/10.1198/016214503000000666; which is hereby incorporated herein by reference in its entirety).

Figure 2:
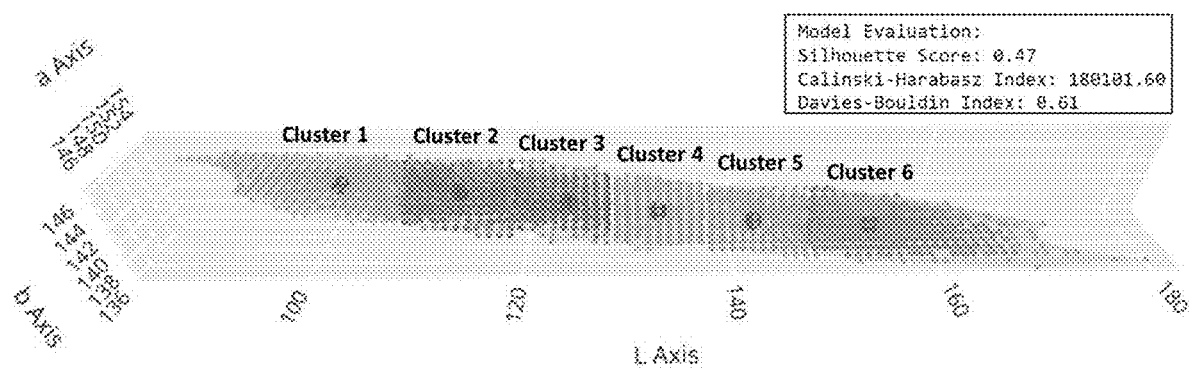
FIG. 2 shows a systematic evaluation and visualization of cluster configurations, according to an embodiment of the subject invention.

Subsequently, the clustering algorithm can be applied to the prepared data. This can involve resizing the LAB color space images, reshaping them for the clustering process, and/or iteratively applying the clustering algorithm until the clusters are optimally formed. The resulting labels, cluster centers can then be calculated, providing a detailed segmentation of the image, as shown in FIG. 2.

The quality of clustering can be rigorously evaluated using established metrics such as the silhouette score, the Calinski-Harabasz Index, and/or the Davies-Bouldin Index. These metrics can provide quantitative assessments of the clustering quality, evaluating aspects such as cluster cohesion, separation, and compactness.

Training can optionally be performed, though this is not necessary and may also be described as fitting or running the unsupervised algorithm or that the algorithm converged to a solution.

Figure 3:
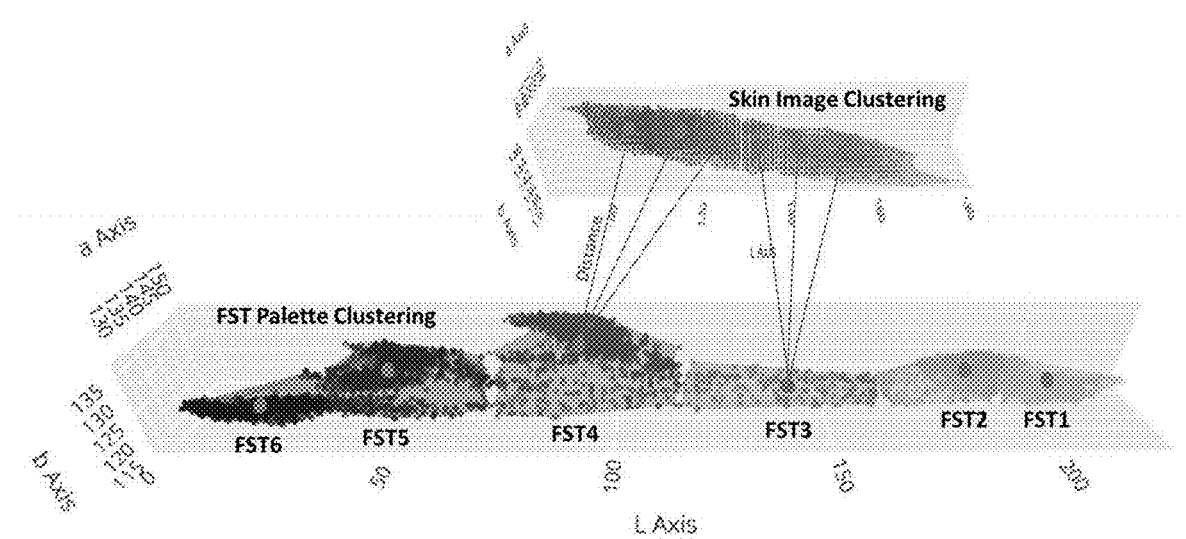
FIG. 3 shows an illustrative scheme of color matching methodology, according to an embodiment of the subject invention.

Match cluster centers with FST palette: An important phase can involve the precise alignment of cluster centers from segmented skin images with the cluster centers of the FST color palette. This process can determine the closest correspondences between the identified cluster centers of skin colors and those of the FST palette, as shown in FIG. 3.

The first step can include quantifying the perceptual differences between each color in the skin palette (represented by cluster centers) and the colors in the FST palette. This can be achieved by calculating the color distance using a standard metric in colorimetry (e.g., CIE76 Delta-E color distance), which effectively measures the differences between two colors (i.e., cluster centers).

Subsequently, each cluster center from the skin palette can be matched with the nearest cluster center in the FST palette based on the calculated color distances. This matching process can be important in identifying the most similar FST color for each identified skin color, providing a clear and quantifiable measure of their similarity.

Visualize results: The visualization of results, specifically the alignment of cluster centers with the FST palette, can be executed with an advanced and informative approach. This process can include creating visual representations that clearly illustrate the relationship between the segmented skin colors and the FST color palette.

Figure 4:
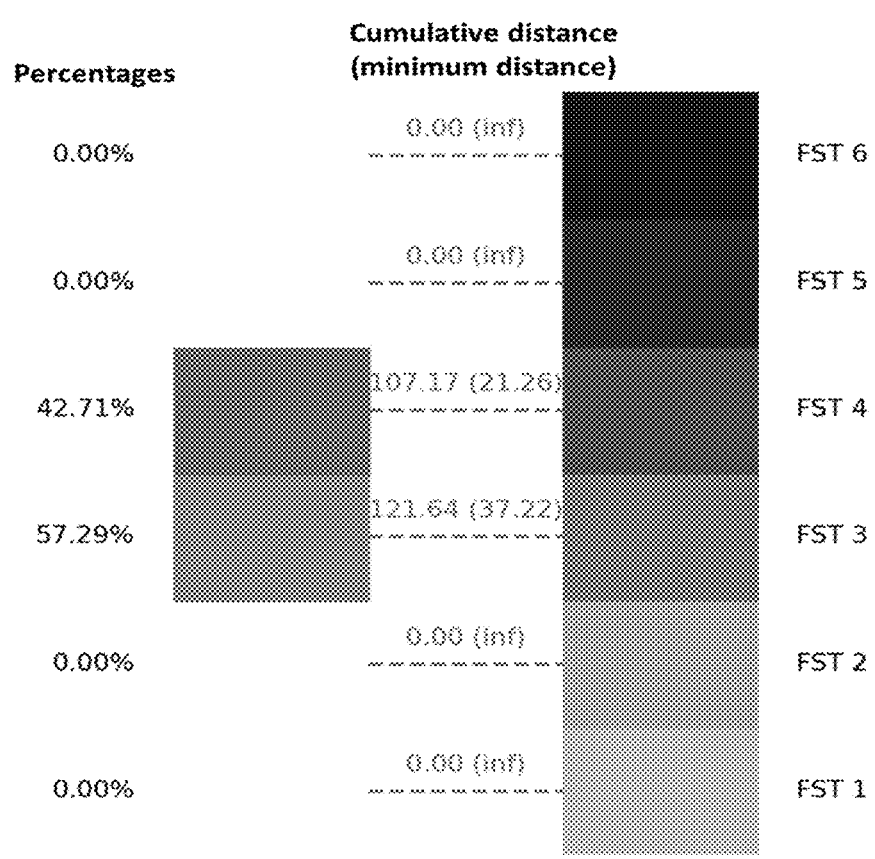
FIG. 4 shows a color alignment visualization between segmented skin colors and Fitzpatrick skin type (FST) palette, according to an embodiment of the subject invention.

The visualization, as shown in FIG. 4, can be designed to display each color from the skin palette alongside its closest match in the FST palette. In order to enhance the interpretability of these results, the visualizations can include not only the paired colors but also annotations indicating the percentage of each skin color within the image and the distance metrics, which quantify the similarity between the skin and FST colors. The use of color rectangles and connecting lines can provide a clear and intuitive representation of the matches.

Validation: FST ground truth classification can be determined by measurements from a commercial device (e.g., Delfin Skin ColorCatch) (see also; Del Bino et al., Variations in skin colour and the biological consequences of ultraviolet radiation exposure, Br. J. Dermatol. 169 Suppl 3 (2013) 33-40, doi.org/10.1111/BJD.12529; which is hereby incorporated herein by reference in its entirety). This tool can be utilized for the validation of the clustering results against real-world skin color measurements.

Figure 5:
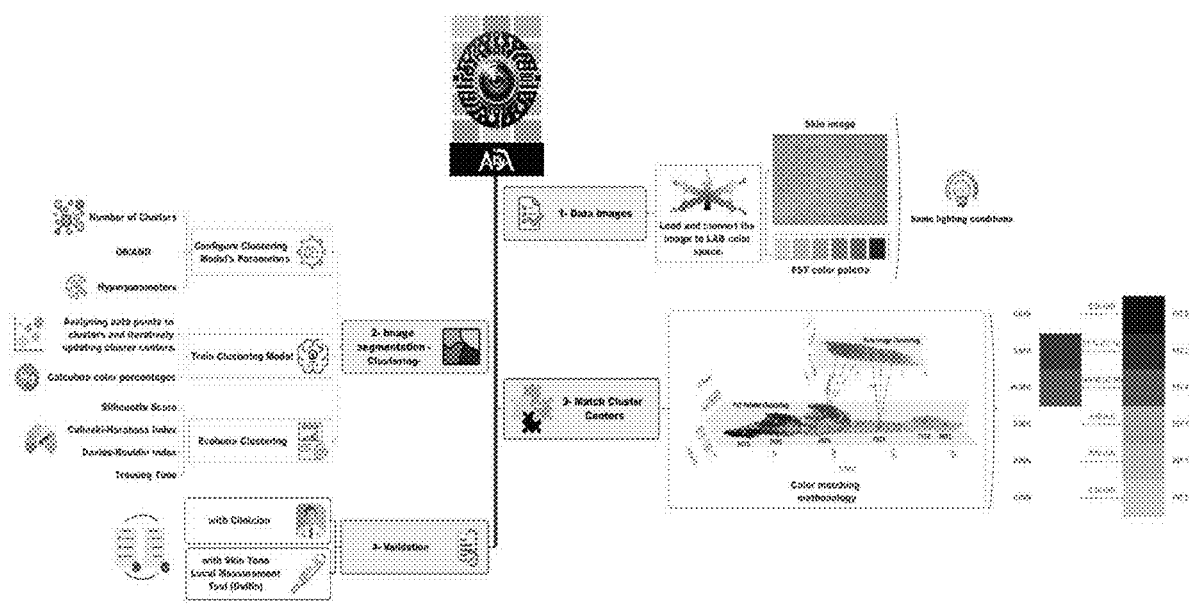
FIG. 5 shows an architecture of a system for classification and/or analysis of skin color(s), according to an embodiment of the subject invention. The system can be referred to herein as Artificial Intelligence Dermatochroma Analytica (AIDA).

End: The process can be concluded with validated and calibrated clustering results ready for practical application and/or further analysis. A comprehensive flowchart detailing a system/method according to an embodiment of the subject invention is shown in FIG. 5.

The utilization of unsupervised learning models in the AIDA system is an important aspect. Unsupervised learning, in contrast to its supervised counterpart, does not rely on pre-labeled data, making it uniquely suited for discovering hidden patterns in complex datasets, such as those encountered in skin color analysis. Within this framework, diverse arrays of clustering models can be employed and compared, to evaluate their strengths and limitations to the task of skin color classification. This methodical assessment allows for identification of the most suitable model that can accurately capture the complex nuances of human skin colors. A discussion of various models follows.

K-means clustering algorithms include the K-Means model and its variants, such as K-means-PCA and K-means mini-batch (see also; Jain, Data clustering: 50 years beyond K-means, Pattern Recognit. Lett. 31 (2010) 651-666, doi.org/10.1016/J.PATREC.2009.09.011; and Sinaga et al., Unsupervised K-means clustering algorithm, IEEE Access 8 (2020) 80716-80727, doi.org/10.1109/ACCESS.2020.2988796; both of which are hereby incorporated herein by reference in their entireties). These were evaluated for their effectiveness in segmenting skin color data into coherent groups. These algorithms are key in determining similarities within the dataset, making them a natural starting point for an analysis.

Density-based models, such as DBSCAN, HDBSCAN, and OPTICS, can be scrutinized for their ability to identify clusters based on data point density (see also; Kriegel et al., Density-based clustering, Wiley Interdiscip. Rev. Data Min. Knowl. Discov. 1 (2011) 231-240, doi.org/10.1002/WIDM.30; which is hereby incorporated herein by reference in its entirety). Their performance in recognizing clusters of varying shapes and sizes is particularly relevant to the diverse and complex nature of skin colors.

Hierarchical methods, including techniques such as agglomerative hierarchical clustering, can be comparted to understand their utility in revealing hierarchical structures within skin color data (see also; Murtagh et al., Algorithms for hierarchical clustering: an overview, Wiley Interdiscip. Rev. Data Min. Knowl. Discov. 2 (2012) 86-97, doi.org/10.1002/WIDM.53; which is hereby incorporated herein by reference in its entirety). The ability to visualize data as a tree-like structure can offer valuable insights into the layered complexity of skin color variations.

Probabilistic techniques, principally Gaussian mixture models (GMMs), can be examined for their probabilistic approach to clustering (see also; Bouveyron, Model-based clustering of high-dimensional data: A review, Comput. Stat. Data Anal. 71 (2014) 52-78, doi.org/10.1016/J.CSDA.2012.12.008; which is hereby incorporated herein by reference in its entirety). Their capability in managing overlapping clusters and providing insights into the likelihood of data point associations can be assessed.

Fuzzy logic approaches, such as Fuzzy C-means, can also be considered as part of this comparative analysis (see also; Nayak et al., Fuzzy C-means (FCM) clustering algorithm: A decade review from 2000 to 2014, Smart Innov. Syst. Technol. 32 (2015) 133-149, doi.org/10.1007/978-81-322-2208-8_14/FIGURES/1; which is hereby incorporated herein by reference in its entirety). Their concept of partial membership, where data points can belong to multiple clusters to varying degrees, is a potential fit for the often-ambiguous boundaries of skin color categories.

Other advanced methods such as affinity propagation, mean shift, and spectral clustering can be evaluated for their unique clustering methodologies (see also; Bodenhofer et al., APCluster: an R package for affinity propagation clustering, Bioinformatics 27 (2011) 2463-2464, doi.org/10.1093/BIOINFORMATICS/BTR406; Cheng, Mean Shift, Mode Seeking, and Clustering, IEEE Trans. Pattern Anal. Mach. Intell. 17 (1995) 790-799, doi.org/10.1109/34.400568; and Von Luxburg, A tutorial on spectral clustering, Stat. Comput. 17 (2007) 395-416, doi.org/10.1007/S11222-007-9033-Z/METRICS; all three of which are hereby incorporated herein by reference in their entireties). These models could offer innovative solutions to the challenges posed by skin color classification.

By methodically assessing the strengths and limitations of each clustering model in the context of skin color classification, the most effective and accurate method for dermatological analysis can be determined.

The FST scale, which is widely recognized in the field of dermatology, categorizes human skin colors into six distinct types based on their reaction to ultraviolet (UV) light. This scale has been established as a foundation in both dermatological research and clinical practice. It is instrumental in the assessment of skin cancer risk, the development of personalized treatment plans, and the understanding of various skin conditions. In the AIDA system, the integration of the FST scale serves two primary purposes. First, it is utilized as a standardized benchmark against which the system's skin color classification can be validated and calibrated. This ensures that the outputs of AIDA are aligned with established dermatological standards, facilitating its adoption in clinical settings. Second, the integration is employed to fine-tune the machine learning models within AIDA, ensuring that the classifications produced by the algorithms are not only accurate in a computational sense but also hold significant clinical relevance.

In recognition of the vast diversity inherent in human skin colors and the dynamic nature of ongoing dermatological research, the AIDA system possesses the flexibility to accommodate a variety of skin color scales beyond the traditional FST scale. For the AIDA system, the task is simply a matter of alignment and matching with any chosen scale palette. Such adaptability is deemed important for a multitude of reasons. Primarily, it enables the application of AIDA across diverse geographic and ethnic landscapes, where alternative skin color categorizations may hold greater prevalence or suitability. Further, the relevance and efficacy of the system are maintained, given that emerging research may necessitate the adoption of more advanced or specialized skin color scales.

AIDA is an advanced system for the classification and analysis of skin colors. AIDA can be used for many applications, including identifying and segmenting wounds in diabetic feet. This can include the creation of a robust and reliable methodology, starting from the ground up with data collection and preparation. The process can involve a meticulous approach to gathering and processing photographic data. Following is a discussion of data collection and preparation, followed by an in-depth look at the performance metrics used to evaluate the AIDA system. The comparative analysis of various unsupervised learning models within the AIDA framework is also discussed, as well as a comparison with a supervised learning model, the CNN.

Embodiments of the subject invention provide a significant leap forward in the field of dermatological research, particularly in the classification and analysis of human skin colors. The examples successfully demonstrate the ability of AIDA to overcome the limitations of other skin color classification methods, such as subjective visual assessments and actual image processing systems. By employing unsupervised learning algorithms, AIDA effectively transcends the constraints of conventional approaches, offering a more nuanced and accurate understanding of the complex spectrum of human skin colors.

The AIDA K-means clustering model has superior performance compared to a supervised CNN. AIDA had nearly double the performance rate of CNN in skin color classification, highlighting its efficiency and effectiveness in handling the diversity and complexity inherent in human skin. Further, the inclusion of a tolerance-based evaluation strategy, reflecting realistic clinical scenarios, resulted in an impressive 97% accuracy (versus 87% with CNN), reaffirming the robustness and reliability of AIDA in predicting skin colors within a clinically acceptable range.

The flexibility of AIDA to adapt to various skin color scales, coupled with its integration of the Fitzpatrick 6-color scale, underscores its potential as a versatile tool in dermatology. This adaptability ensures that AIDA remains relevant across diverse geographical and ethnic landscapes, as well as in the light of emerging dermatological research. AIDA's robust design, validated and calibrated through rigorous methodologies and clinician feedback, positions it as a promising solution for a range of dermatological applications, from diagnostic assessments to treatment planning. The efficacy of AIDA in classifying skin colors is notably sensitive to the quality of lighting and the camera used for capturing images. Consistent and appropriate lighting conditions can be equally important, as variations in lighting can significantly impact the perception and representation of skin colors. Maintaining uniform lighting during the image capture process is important to minimize any distortions or inconsistencies in the skin color data. Adherence to these standards can greatly enhance the precision and reliability of AIDA's skin color classification, thereby optimizing its performance in dermatological applications.

Embodiments of the subject invention mark a significant advance in dermatological technology. The innovative approach of combining advanced machine learning techniques with dermatological expertise sets a new standard for skin color analysis. AIDA provides more accurate, efficient, and personalized dermatological care.

Embodiments of the subject invention provide several advantages over state-of-the-art methods in skin color classification and dermatological diagnostics, including improved accuracy and efficiency, elimination of labeling requirement, robustness under variable conditions, adaptability to different skin color scales, enhanced personalized care, cost-effectiveness, and advanced integration capabilities. With respect to improved accuracy and efficiency, AIDA significantly outperforms traditional supervised models like CNNs in skin color classification, achieving a higher performance rate (nearly twice that of CNNs) and demonstrating a predictive accuracy of 97% compared to 87% for CNNs using a tolerance-based approach. This showcases AIDA's ability to handle the diversity and complexity of skin colors with greater precision. With respect to elimination of labeling requirement, unlike supervised learning models that rely heavily on labeled datasets, AIDA leverages unsupervised learning. This eliminates the need for extensive and often labor-intensive data labeling, reducing the time and resources required for model training and updating. With respect to robustness under variable conditions, AIDA is designed to overcome the limitations posed by environmental factors that traditionally affect the accuracy of skin color analysis. By using advanced clustering and matching techniques, AIDA can accurately classify skin colors even under variable lighting conditions, making it more reliable for practical dermatological applications. With respect to adaptability to different skin color scales, AIDA is not limited to a specific skin color scale. Its flexibility allows for alignment with various dermatological standards, including the FST scale, making it versatile and applicable across diverse geographic and ethnic contexts. With respect to enhanced personalized care, by providing more accurate and detailed classification of skin colors, AIDA paves the way for more personalized dermatological treatment planning. This can lead to better-targeted therapies, improved patient outcomes, and a more nuanced understanding of skin-related conditions and their treatments. With respect to cost-effectiveness, the efficiency and automation offered by AIDA can reduce the need for manual intervention and the reliance on expensive diagnostic equipment. This can lead to cost savings for both healthcare providers and patients, making advanced dermatological diagnostics more accessible. With respect to advanced integration capabilities, AIDA's modular architecture enables seamless integration with existing dermatological diagnostic tools and electronic health records (EHRs), facilitating a more comprehensive approach to patient care.

Embodiments of the subject invention have many uses, including dermatological diagnostics, personalized treatment planning, research and development, enhanced skin cancer screening, integration with wearable and mobile health technologies, customized skincare and cosmetic products, telemedicine and remote diagnostics, cross-disciplinary applications, and training and education. With respect to dermatological diagnostics, AIDA can be used to enhance the accuracy of skin color classification, facilitating more precise diagnostics in dermatology. This is crucial for conditions where skin color plays a significant role in diagnosis, such as diabetic foot wound, pigmentary disorders, and melanoma. With respect to personalized treatment planning, by providing a more accurate classification of skin colors, AIDA enables dermatologists to tailor treatment plans more effectively to individual patients. This can improve the efficacy of treatments for various skin conditions and cosmetic procedures. With respect to research and development, in the field of dermatological research, AIDA's capabilities allow for more detailed and accurate data collection regarding skin color diversity. This can contribute to the development of new treatments and the understanding of how skin conditions affect individuals differently based on skin color. With respect to enhanced skin cancer screening, with its precision in skin color classification, AIDA can play a critical role in the early detection and screening of skin cancers. By integrating AIDA with imaging technologies, dermatologists can identify malignant lesions more accurately across different skin types. With respect to integration with wearable and mobile health technologies, AIDA can be integrated into wearable devices and/or smartphone applications, allowing for real-time monitoring of skin conditions and/or changes in skin color. This can revolutionize the way skin health is managed, offering personalized advice and early warning signs for potential issues. With respect to customized skincare and cosmetic products, the cosmetic industry can use AIDA to create more inclusive and personalized skincare and beauty products. By understanding the nuances of skin colors, companies can develop products tailored to a wider range of skin types, improving effectiveness and customer satisfaction. With respect to telemedicine and remote diagnostics, AIDA can significantly enhance telemedicine services by providing accurate skin color analysis through digital images. This can improve the quality of remote consultations, making dermatological care more accessible to patients in remote or underserved regions. With respect to cross-disciplinary applications, beyond dermatology, AIDA can be applied in forensic science, anthropological research, and the development of prosthetics and medical devices, ensuring these are appropriately color-matched to individuals' skin tones for better aesthetics and acceptance. With respect to training and education, AIDA can be a valuable tool for educational purposes, helping medical students and professionals to better understand the diversity of skin colors and how it affects the diagnosis and treatment of various conditions.

Embodiments of the subject invention provide a focused technical solution to the focused technical problem of how to address the inherent diversity and complexity of skin colors in skin color classification. The solution is provided by utilizing an unsupervised AI learning model for the alignment of segmented skin image clusters with the Fitzpatrick color scale clusters. Embodiments of the subject invention provide many advantages, including to ability to improve a computer system being used for skin color classification by efficiently performing the detection compared to related art systems (e.g., via a reduced processing time) (this can free up memory and/or processor usage).

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data.

Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When the term module is used herein, it can refer to software and/or one or more algorithms to perform the function of the module; alternatively, the term module can refer to a physical device configured to perform the function of the module (e.g., by having software and/or one or more algorithms stored thereon).

When ranges are used herein, combinations and subcombinations of ranges (including any value or subrange contained therein) are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Materials and Methods

Data Collection and Preparation: Diabetic foot ulcers (DFUs) are a concerning issue for diabetics as the healing process for these patients is largely compromised. Healing tissue requires oxygen for energy production and tissue remodeling mechanisms. A smartphone-based near-infrared (NIR) imaging device was developed inhouse, which is capable of extracting tissue oxygenation maps in a noncontact manner to visualize the underlying physiology (see also; Leizaola et al., Deep learning algorithms to classify Fitzpatrick skin types for smartphone-based NIRS imaging device, Https://Doi.org/10.1117/12.2665179 12516 (2023) 12-17, doi.org/10.1117/12.2665179; which is hereby incorporated herein by reference in its entirety). The device was used to evaluate the healing process of DFUs by using white light images and tissue oxygenation maps. However, skin color can affect the tissue oxygenation maps because melanin (component causing skin color) is a large absorber of NIR light. Hence, a long-term goal could be to implement a correction technique on the device for more accurate spatial analysis with the consideration of skin color. As an initial step, a study conducted at Florida International University (FIU) focused solely on capturing white light data from subjects using the mentioned device (which can be referred to herein as SPOT) to determine the appropriate model for skin color classification.

Recruitment involved 48 control (without wounds) subjects, across Fitzpatrick skin types (FST I through FST VI). Subjects were positioned in a seated and supine posture with their foot exposed for imaging. A reference sticker with the six FST colors, from a scale commonly used by dermatologists, was placed visibly within the imaging field of view (see also; Ho et al., Color bar tool for skin type self-identification: A cross-sectional study, J. Am. Acad. Dermatol. 73 (2015) 312-313, doi.org/10.1016/j.jaad.2015.05.024; which is hereby incorporated herein by reference in its entirety). For a consistent background during SPOT data collection, a black curtain was placed to separate the subject's foot and knee.

Subjects were imaged on seven locations of the foot to encompass all regions where a DFU could develop and each under three lighting conditions, respectively. The top-foot location under one lighting condition (color temperature of 4100 Kelvin (K)) was considered for proof-of-concept of the model. Environmental lighting conditions were controlled, and image settings were also controlled to ensure the sole variable evaluated by the algorithm is skin color. The inhouse device was controlled via an in-house application that fixated the focus, white balance, and exposure of the camera for no color variability. Locked imaging settings were required because the appearance of the skin color was affected by the phones auto-adjustment image settings. Additionally, the application was utilized for imaging distance (maintained at 10 centimeters (cm)+/−0.5 cm from the foot region) and data/image capture in RGB format.

Figure 11A:
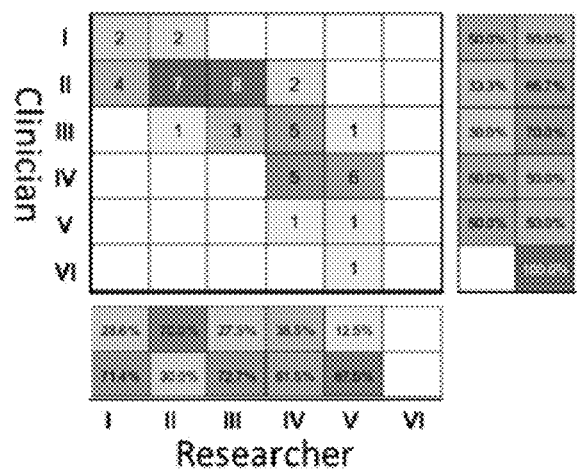
FIGS. 11A-11C show confusion matrix comparison of three ground truth methods that could be used for testing an unsupervised CNN model from 48 images.
Figure 11B:
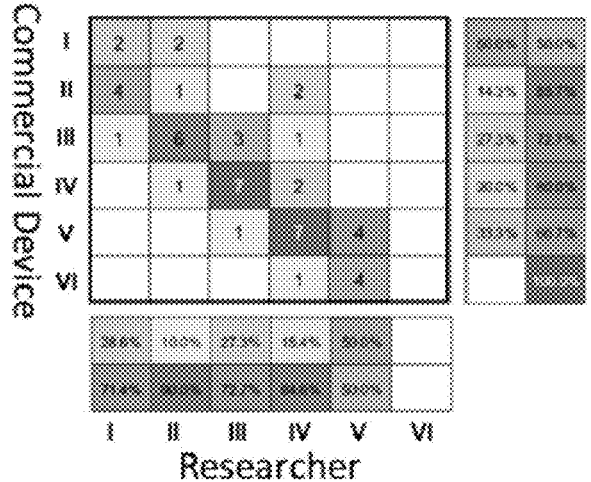
Figure 11C:
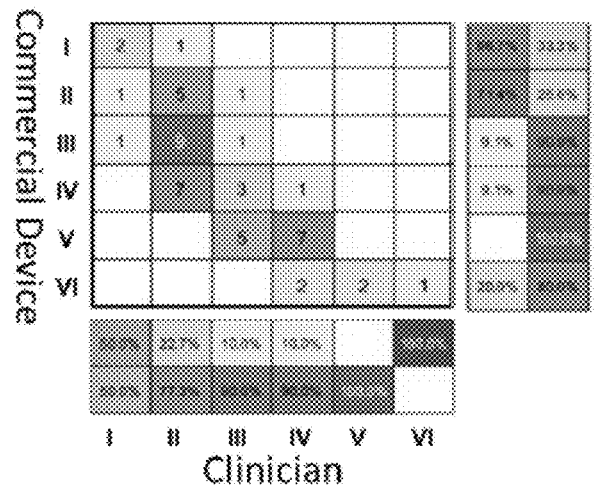

The goal was to determine an efficient approach to skin color classification because the current method of visual classification by a human operator can be subjective and time-consuming. However, a comparison was done of the classification by two humans (a researcher and a clinician) and a commercial device (Delfin Skin ColorCatch) for consistency purposes. The possible ground truths (GTs) available were compared to determine the variability among classifications. The subjectivity in the researcher and clinician classification was evident when compared to each other by a large variability, as seen in FIGS. 11A-11C. Importantly, the commercial device did not align exactly with either human classification. The researcher classification showed to have a pattern of underestimation (lighter skin type) in FST when compared to the commercial device. In continuation, an error of >50% was noted across FSTs when the clinician classification was compared to the commercial device and there was no distinct pattern, as shown in FIGS. 11A and 11B. The human-intervened classifications had a concentration between FST 2-3 and utilized the entire image as the skin. On the other hand, the commercial device took three measurements at a point (for each respective foot location) without an interference of external light (i.e., not affected by lighting changes). The subjective nature of the human classification led to the use of the commercial device as GT due to the unbiased systematic approach. The point measurement of the device calculated the individual topological angle (ITA) and was subsequently converted to FST using a known approach (see also; Chardon et al., Skin colour typology and suntanning pathways, Int. J. Cosmet. Sci. 13 (1991) 191-208, doi.org/10.1111/J.1467-2494.1991.TB00561.X; which is hereby incorporated herein by reference in its entirety).

Performance metrics: In the evaluation of AIDA clustering system, the incorporation of various performance metrics is important for a rigorous assessment of the clustering models. The performance metrics utilized included Silhouette score, Calinski-Harabasz (C-H) index, Davies-Bouldin (D-B) index, and clustering time.

The Silhouette score can be calculated using the formula:

$$S(i) = \frac{b(i) - a(i)}{\max\{a(i), b(i)\}} \quad (1)$$

where $S(i)$ is the Silhouette score, $a(i)$ is the average distance from the $i^{th}$ data point to the other points in the same cluster, and b(i) is the smallest average distance from the $i^{th}$ data point to points in a different cluster, minimized over all clusters (see also; Rousseeuw, Silhouettes: A graphical aid to the interpretation and validation of cluster analysis, J. Comput. Appl. Math. 20 (1987) 53-65, doi.org/10.1016/0377-0427 (87) 90125-7; which is hereby incorporated herein by reference in its entirety).

This score, ranging from −1 to +1, is employed as a metric to determine the degree of similarity an object holds within its own cluster in comparison to other clusters. Higher values of the Silhouette score indicate a strong match to the respective cluster and a poor match to neighboring clusters. The applicability of this metric in AIDA facilitated the evaluation of cluster cohesion and separation.

The C-H index is defined by the formula:

$$CH(k) = \frac{B(k)/(k-1)}{W(k)/(n-k)} \quad (2)$$

where CH(k) is the C-H index, B(k) is the between-group dispersion matrix and W(k) is the within-cluster dispersion matrix for k clusters, and n is the number of data points (see also; Wang et al., An improved index for clustering validation based on Silhouette index and Calinski-Harabasz index, IOP Conf. Ser. Mater. Sci. Eng. 569 (2019) 052024, doi.org/10.1088/1757-899X/569/5/052024; which is hereby incorporated herein by reference in its entirety).

Also known as the Variance Ratio Criterion, this index is a measure of the dispersion between and within clusters. Elevated scores on this index suggest more distinct clustering. The C-H index was utilized to quantify the distinctiveness of color clusters within AIDA.

The D-B index is determined using:

$$DB = \frac{1}{n}\sum_{i=1}^{n} \max_{i \neq j}\left(\frac{\delta(c_i, c_j)}{\Delta(c_i) + \Delta(c_j)}\right) \quad (3)$$

where DB is the D-B index, $\delta(c_i, c_j)$ represents the distance between centroids of clusters i and j, and $\Delta(c_i)$ is the average distance of all points in cluster i to the centroid $c_i$ (see also; Tomašev et al., Clustering evaluation in high-dimensional data, Unsupervised Learn. Algorithms (2016) 71-107, doi.org/10.1007/978-3-319-24211-8_4/FIGURES/35; which is hereby incorporated herein by reference in its entirety).

This index, a function of the ratio of within-cluster to between-cluster distances, is indicative of the compactness and separation of clusters. Lower values of the index are indicative of better clustering. The D-B Index was employed to provide an overview of the partitioning effectiveness of color data in AIDA.

Clustering time is measured as the elapsed time required for the system to cluster the data. It can be recorded, for example, in seconds. The computational efficiency of AIDA was evaluated through the measurement of the time taken, ensuring its suitability for real-time applications in clinical environments.

Each of these metrics provided quantitative measures to assess the effectiveness, efficiency, and accuracy of the clustering algorithms in categorizing skin colors, ensuring a robust and objective analysis.

Example 1—Comparative Analysis of Clustering Models

Figure 6:
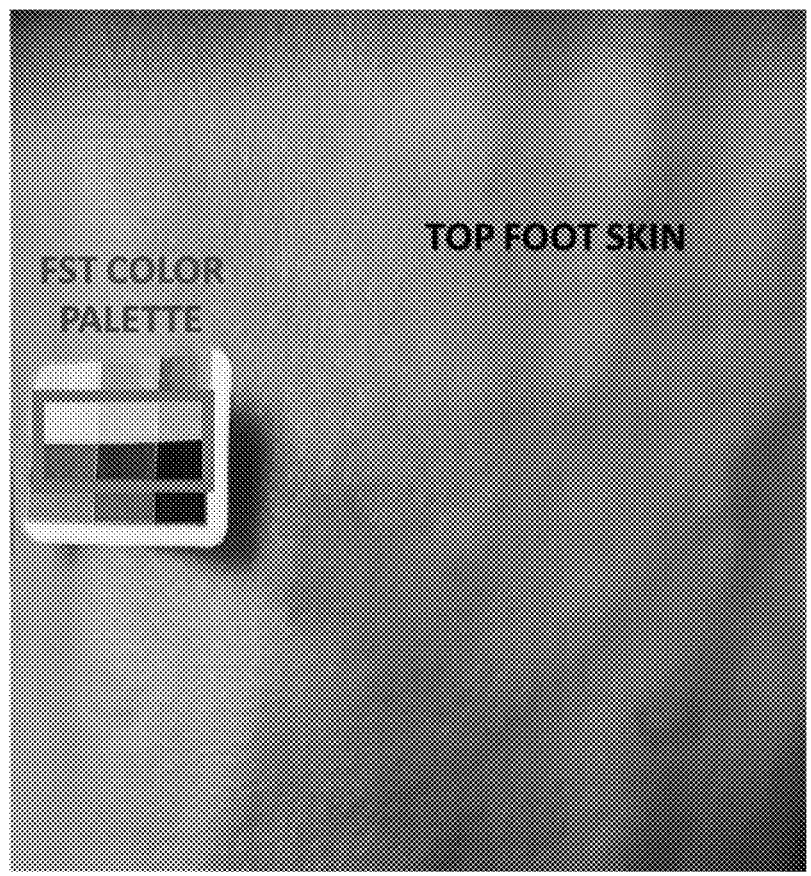
FIG. 6 shows an image of a sample of top foot skin and FST scale palette imagery used in a comparative study of clustering models.

A comparative analysis was conducted of different unsupervised learning models within the AIDA framework, and a systematic evaluation was undertaken using the performance metrics stated previously (i.e., Silhouette score, C-H index, D-B index, and clustering time). The models under consideration included standard K-means, K-means mini-batch, K-means-PCA, DBSCAN, HDBSCAN, OPTICS-DBSCAN, agglomerative hierarchical clustering (AHC), Gaussian mixture models (GMM), fuzzy C-means, affinity propagation, mean shift, and spectral clustering. A specific subset from the collected dataset was selected for this comparative analysis. This subset comprised two key images: one representing the skin color (top-foot location) of the human subject; and the other featuring the FST palette scale used for the matching (FIG. 6). These images were chosen to provide a focused and representative sample for evaluating the performance of various clustering models, thereby enabling a precise and targeted analysis within the broader dataset.

Figure 7A:
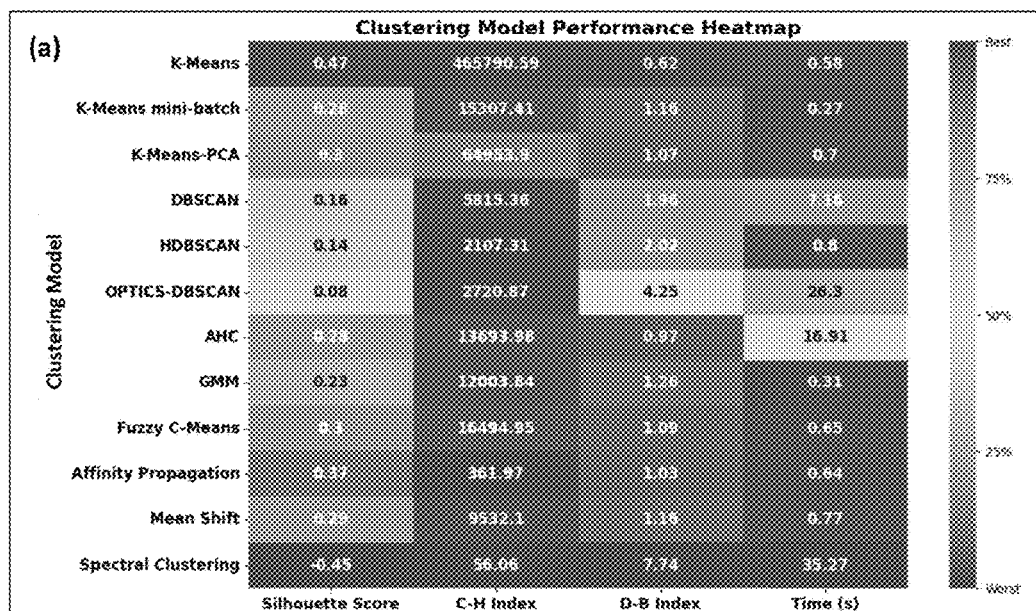
FIGS. 7A and 7B show comparative visualizations of clustering model performances in an AIDA system, according to an embodiment of the subject invention.
Figure 7B:
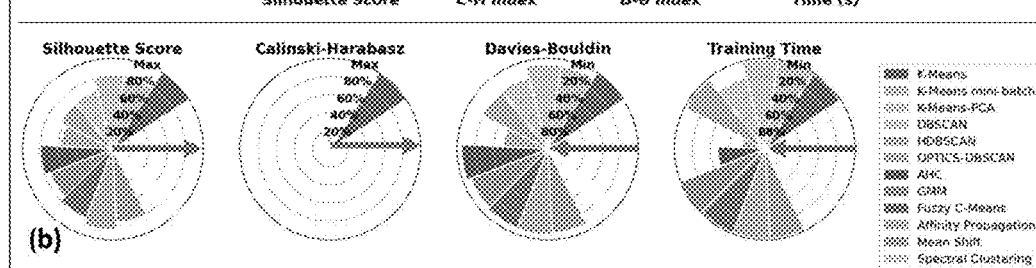

The comparative performance analysis of the clustering models is depicted in FIGS. 7A and 7B.

K-means type models: K-means demonstrated superior performance with a higher Silhouette score (0.47) and C-H index (465790) compared to K-means mini-batch and K-means-PCA, indicating better cluster quality and separation. However, K-means mini-batch had a shorter clustering time (0.27 seconds(s)), suggesting greater computational efficiency, albeit at the cost of clustering quality. K-means-PCA, an extension of K-means with dimensionality reduction, showed a moderate silhouette score and C-H index (0.28 and 15307, respectively), suggesting decent clustering but not as effective as standard K-means. The incorporation of PCA appeared to slightly increase the clustering time (0.7 s) compared to basic K-means.

DBSCAN type models: DBSCAN and HDBSCAN, both density-based models, exhibited lower scores across all performance metrics compared to K-means. Their lower Silhouette scores (≤0.16) indicate less distinct clustering, which might be due to the complex nature of skin color data not conforming well to density-based clustering. OPTICS-DBSCAN performed poorly in comparison to other models, with the lowest Silhouette score and the highest D-B index (0.08 and 4.25, respectively), indicating poor clustering quality and separation. Its significantly longer clustering time (26.3 s) also makes it less desirable for real-time application.

AHC: AHC showed moderate performance (Silhouette score of 0.28) but required significantly more time for clustering (16.91 s), making it less suitable for scenarios where time is crucial.

GMM: GMM presented a balance between cluster quality (with a Silhouette score of 0.23) and clustering time (0.31 s) but did not excel in any particular metric.

Fuzzy C-means: Fuzzy C-means, allowing for overlapping clusters, showed reasonable performance (with a Silhouette score of 0.3), suggesting its potential applicability in situations where skin colors do not distinctly belong to separate categories.

Affinity Propagation and Mean Shift: Both these models demonstrated moderate to high silhouette scores (with a Silhouette score of 0.37 for affinity propagation and 0.29 for mean shift) but were not as effective as K-means in overall clustering performance.

Spectral Clustering: Spectral Clustering was found to be the least suitable for this application, evidenced by its negative Silhouette score (−0.45) and the longest clustering time (35.27 s), indicating poor clustering effectiveness and computational inefficiency.

In summary, standard K-means emerged as the most effective model for skin color classification in the AIDA system, offering a balance between clustering quality and computational efficiency. While other models like K-means mini-batch and fuzzy C-means showed potential in specific contexts, their overall performance was outshined by K-means. The comparative analysis underscores the importance of selecting a model that not only provides accurate clustering but also aligns with the practical requirements of speed and efficiency in a clinical setting.

Example 2—Comparison with Supervised Learning Model

A critical comparative analysis was conducted between the best unsupervised clustering model (i.e., K-means model) and a supervised learning model, specifically the CNN. This comparison encompassed the entire dataset of 48 human subjects, providing a comprehensive understanding of the performance dichotomy between these two approaches in the context of skin color classification.

The primary criterion for comparison was the accuracy of classification against the ground truth data (Delfin Skin ColorCatch). The effectiveness of both the unsupervised clustering model and the CNN was measured by how closely their classification of the dataset aligned with this predefined ground truth.

The K-means clustering models was first applied to the dataset. The K-means model classified the skin colors of the 48 subjects without prior labeling, relying solely on the inherent patterns and characteristics identified within the data. In parallel, a CNN model was trained and then used to classify the same dataset. The CNN was pre-trained with labeled data (Delfin Skin ColorCatch) to recognize and classify skin colors.

Both methodologies were then evaluated on their accuracy, with their results compared to the ground truth data. The evaluation metric was the classification accuracy, which was calculated as the percentage of correctly classified instances out of the total instances. Other classification metrics such as precision, recall, and F1-score were also considered to provide a holistic view of the models' performance.

Data preprocessing and augmentation for CNN: A comprehensive approach was adopted for data preprocessing and augmentation for the CNN used in skin color classification. This process involved several image manipulation techniques to enhance the diversity and quality of the dataset, ensuring robust training and evaluation of the CNN model.

Two key image preprocessing steps were employed to enhance skin color analysis. First, a function cropped out white borders by converting images to grayscale, thresholding for white regions, and then cropping to the largest contour's bounding box. Second, white frames were removed using advanced morphological operations and contour detection, ensuring only relevant skin color information was retained. These steps were pivotal in focusing on essential skin areas and eliminating irrelevant content.

In order to increase the dataset's variability and simulate different real-world conditions, several augmentation techniques were applied. These included rotating images at random angles, random horizontal shifts for variability in color positioning, and random vertical shifts for variability in color positioning. Additionally, random zooming simulated varying camera-subject distances, while horizontal and vertical flipping diversified the dataset by mirroring skin presentations. A batch augmentation process was developed to systematically apply these techniques, generating multiple augmented versions of each image. This expanded the dataset significantly, with the augmented images saved for use in model training and validation.

In order to tackle the issue of uneven FST distribution in the dataset, an oversampling technique was used to ensure a fair representation for each FST. This expanded the dataset to include 1,000 subject images for every FST. This approach addressed the class imbalance in the training data. The combination of these preprocessing and augmentation techniques resulted in a richly varied and high-quality dataset, crucial for the effective training of the CNN model.

Architecture and training of CNN model: After data augmentation, each image was resized to 64×64 pixels to standardize the input size and ensure faster training. Images were also normalized by dividing pixel values by 255, converting them into a range of 0 to 1. Skin colors were labeled based on the FST class given by Delfin Skin ColorCatch, providing a reliable ground truth for training the CNN.

Figure 8:
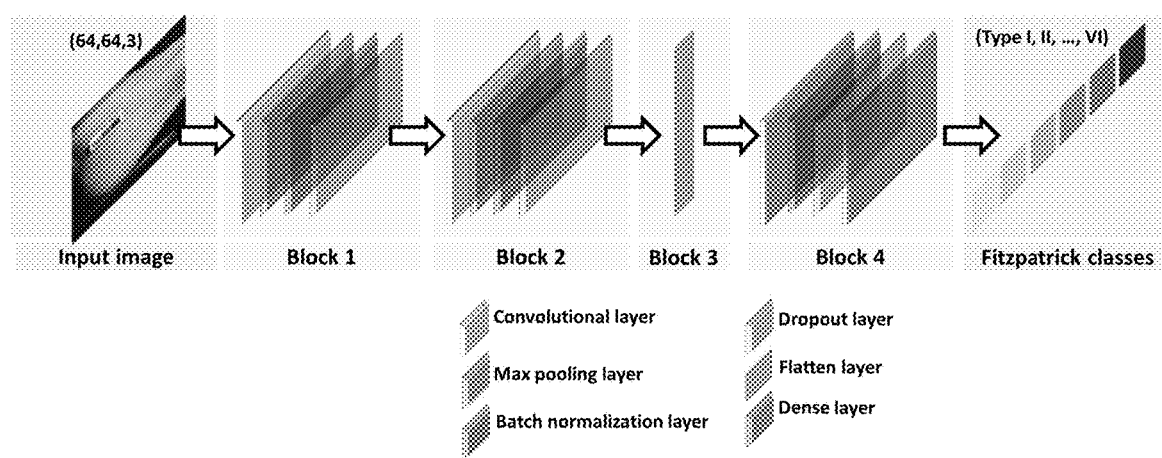
FIG. 8 shows an architecture of a convolutional neural network (CNN) model used in a comparative analysis.

The CNN model, which is shown in FIG. 8, included multiple convolutional layers with MaxPooling and BatchNormalization. These layers are instrumental in extracting features from the images. Dropout and L2 regularization were used to inhibit or prevent overfitting, ensuring the model's generalizability to new, unseen data. The model concluded with dense layers, including a final SoftMax layer for classification, which maps the extracted features to the respective skin color categories. A Bayesian Optimization approach was used to find the best hyperparameters for the CNN. This included optimizing the number of filters, kernel size, dropout rates, and regularization parameters in convolutional and dense layers.

Early stopping and reduce learning rate on Plateau were used as callbacks to enhance the training process, preventing overfitting, and adjusting the learning rate for optimal convergence. The CNN was trained on the prepared dataset, with the validation set used to monitor the model's performance and inhibit or prevent overfitting. During the training phase, 24 subjects were initially utilized, while the remaining 24 were set aside for testing the model's performance on untrained data, for comparison with AIDA (see also the table in FIG. 13). Employing extensive data augmentation techniques, the 24 subject images were expanded to 6000, featuring 1000 images per FST category. In the training process, 70% of the available data was allocated for training the convolutional neural network (CNN). The remaining 30% was strategically divided between validation and test sets to assess the model's performance and generalization capabilities. The CNN model was precisely defined with specific hyperparameters, and Bayesian Optimization was employed to search for the optimal configuration. Subsequently, the CNN was trained on the augmented and balanced training set, incorporating early stopping and learning rate reduction for effective convergence. Overall, the training process involved feeding the augmented and balanced dataset into the CNN model.

After training, the model was evaluated on the test set to determine its accuracy and effectiveness in classifying skin colors.

Figure 9:
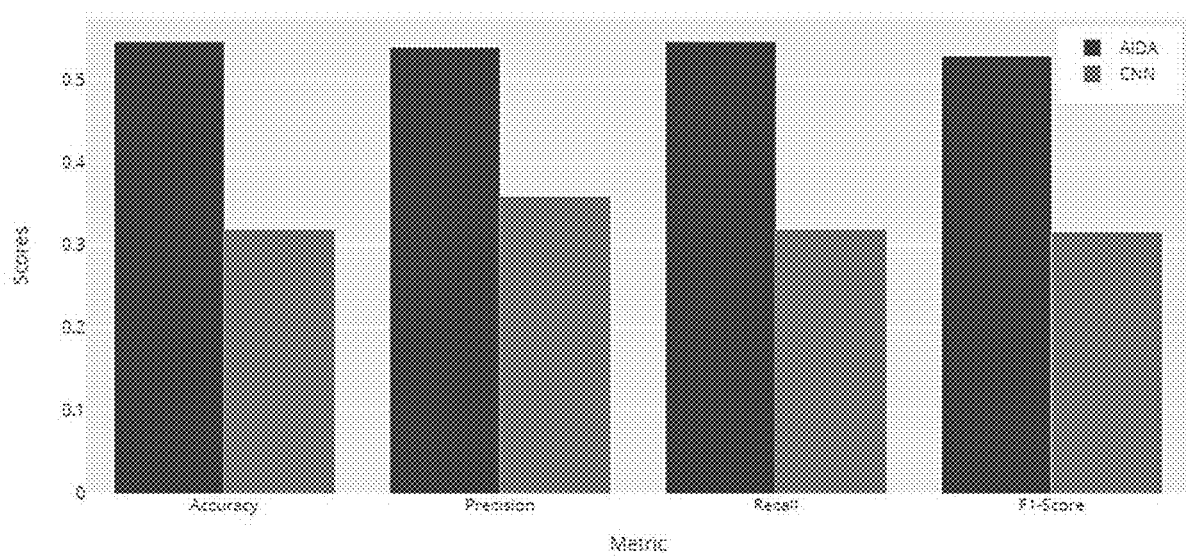
FIG. 9 shows bar charts for the evaluation of K-Means (AIDA) versus CNN performances in skin color classification. For each bar chart (accuracy, precision, recall, and F1 score), the left (blue) bar chart is for AIDA, and the right (red) bar chart is for CNN.

Evaluation of K-Means (AIDA) versus CNN performance in skin color classification: The evaluation analysis conducted within the context of the AIDA project comparing the performance of the K-means clustering algorithm (AIDA) and CNN model, yielded notable results. The assessment focused on the accuracy, precision, recall, and F1-Score of both models in classifying skin colors against the ground truth data. The results are shown in FIG. 9.

The AIDA system demonstrated strong performance in skin color classification with an accuracy of 0.56, indicating that it correctly identified more than half of the skin colors when compared to the ground truth data. This level of accuracy suggests a notable capability of the model in accurately predicting skin color categories. The precision of AIDA, which assesses the proportion of true positives among all positive predictions, was recorded at 0.54. This precision score implies a reasonably good tendency of the model to correctly classify skin colors when it predicts a specific category. Further, the recall for AIDA was measured at 0.54, signifying that the model correctly identified approximately 54% of all relevant instances as per the ground truth. This recall score underscores the model's effectiveness in detecting true positives. The F1-Score, a critical metric that combines precision and recall, was 0.53 for AIDA. This score highlights a balance between precision and recall, while also leaving room for enhancement of the overall accuracy and reliability. These results reflect the proficiency of the AIDA system in classifying skin colors, with its performance metrics demonstrating a substantial degree of accuracy, precision, and recall in line with the objectives of the study.

The CNN model demonstrated an accuracy of 0.32, meaning that only 32% of the classifications matched the ground truth data. This lower accuracy indicates significant challenges in the model's ability to correctly classify skin colors. With a precision score of 0.36, the CNN showed a lower likelihood of correct positive predictions compared to AIDA. This lower precision points towards a higher rate of false positives in the CNN's classifications.

The recall for the CNN was 0.32, which means it correctly identified 32% of all relevant instances. This lower recall score indicates a reduced sensitivity in detecting true positives. The F1-Score for the CNN was 0.31, significantly lower than AIDA's score. This lower F1-score reflects a suboptimal balance between precision and recall, emphasizing the model's limitations in both aspects.

The comparative evaluation revealed that the K-means clustering algorithm used in AIDA outperformed the CNN model across all metrics. While AIDA demonstrated moderate effectiveness in classifying skin colors, the CNN model exhibited notable challenges, evident in its lower accuracy, precision, recall, and F1-score. These results underscore the potential of AIDA in effectively handling complex tasks like skin color classification, especially when compared to traditional supervised approaches like CNNs.

Figure 10:
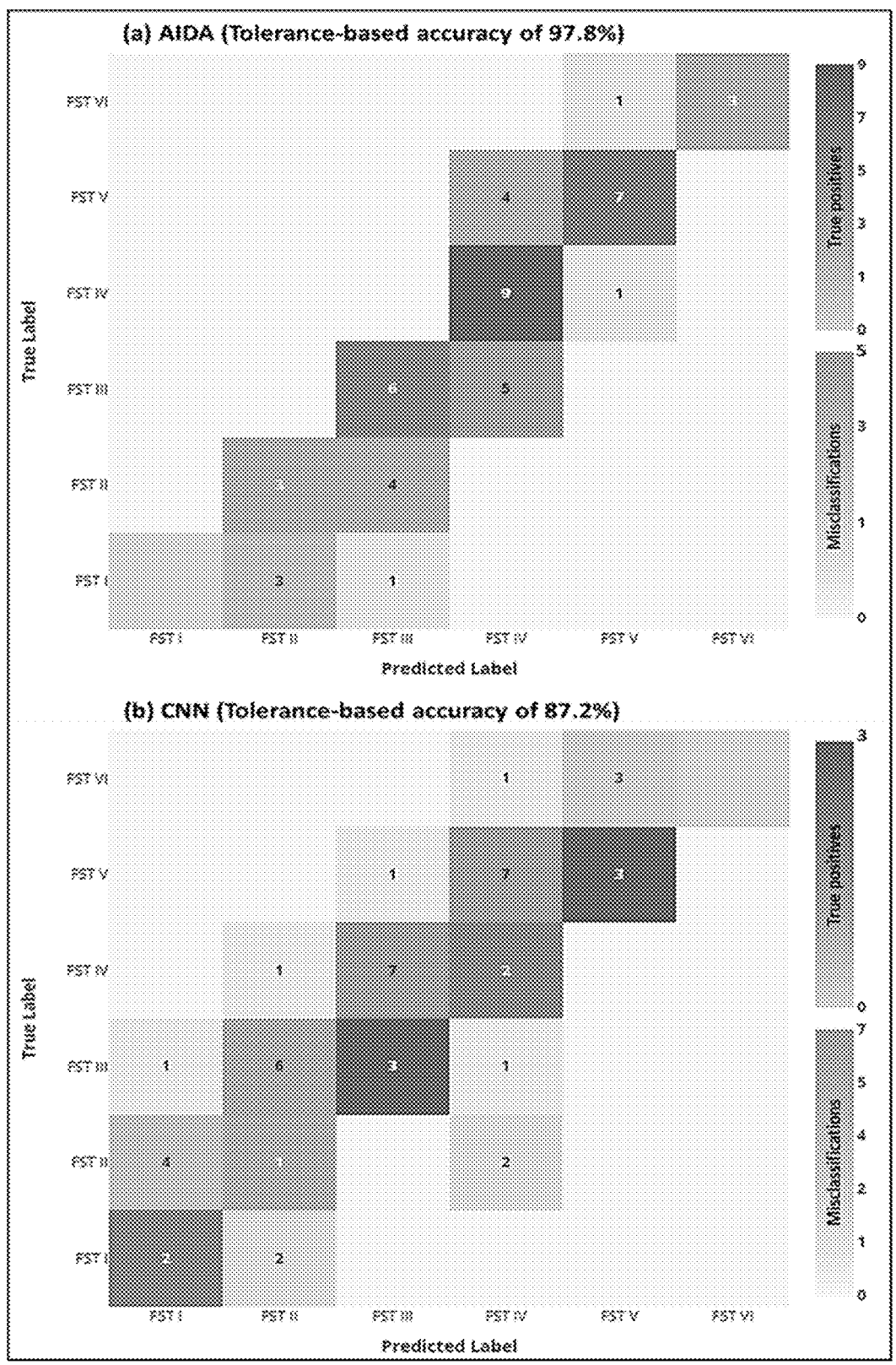
FIG. 10 shows a tolerance-based comparative analysis of AIDA and CNN predicted outcomes versus ground truth data points. The true values are shown in the top chart (labeled "Ground truth frequency"), and the predicted values are shown in the other two charts (labeled "Predicted FST Values" for AIDA and "Predicted FST Values" for CNN).

Example 3—Performance Analysis of AIDA Versus CNN in Predicting Skin Colors with Tolerance Adopting a practical approach with a +/−1 tolerance level for predictions revealed another significant distinction between the two models, as shown in FIG. 10. AIDA achieved a remarkable tolerance-based accuracy of 97%, showcasing its consistency and reliability within a clinically acceptable margin of error. In contrast, the CNN model attained an 87% accuracy under the same criteria. This difference underscores AIDA's enhanced capability to match the ground truth values more closely.

The visualizations further supported this finding, with AIDA's predictions displaying a tighter concentration around the perfect prediction line, especially within the +/−1 deviation band. This contrasted with the CNN's broader distribution, as seen in both the scatter plots and the histograms. The performance with a +/−1 tolerance highlights AIDA's robustness in predicting FST colors, affirming its superiority over the CNN model. AIDA not only excels in exact match accuracy but also demonstrates greater adaptability and precision in a clinical context, where a margin of tolerance is often necessary.

The comprehensive evaluation reveals AIDA's potential as a more effective tool for dermatological assessments and research into skin color classification. Its higher tolerance-based accuracy reflects AIDA's advanced predictive capabilities, making it a preferred choice for applications requiring nuanced skin color analysis.

Based on the comprehensive analysis conducted within the AIDA framework, significant steps have been taken towards enhancing the precision and efficiency of skin color classification in dermatological diagnostics. A diverse array of unsupervised learning models were evaluated, shedding light on the nuanced performance differences that substantially impact their applicability and effectiveness in real-world scenarios. The robustness of the standard K-means clustering model was underscored by its superior performance, evidenced by higher Silhouette scores and C-H indexes. This superior performance is attributed to several key factors. The perceptual uniformity of the LAB color space is conducive to the Euclidean distance measure utilized by K-means, ensuring that the visual importance of color changes is consistently maintained. Further, the distribution of skin colors, which often naturally form compact clusters, aligns well with the spherical clustering tendency of K-means. The algorithm's reliance on centroids for defining clusters is particularly advantageous for representing typical skin tones, a feature that holds significant value in dermatological diagnostics. The computational efficiency of K-means, along with its resilience to lighting variations of the LAB color space, which are critical in dermatological analysis, also stand out. However, the trade-off between efficiency and quality when using K-means mini-batch and the minimal impact of PCA integration on performance improvements could warrant further scrutiny. Lower performance of density-based models (DBSCAN, HDBSCAN, and OPTICS-DBSCAN) and long clustering times associated with certain models (e.g., spectral clustering) have been highlighted, emphasizing the challenges of applying these approaches to skin color classification. The importance of model selection in accordance with specific dataset characteristics, such as dimensionality, data distribution nature, and available computational resources, has been emphasized. A potential avenue for applications where skin colors exhibit a high degree of variability and do not fit neatly into distinct categories has been suggested by the reasonable performance of fuzzy C-means, which allows for overlapping clusters. This opens the door to more nuanced and flexible approaches to skin color analysis, reflecting the complex and varied nature of human skin tones.

A comparative analysis was conducted to assess the efficacy of the AIDA clustering and matching algorithm against that of a CNN model in the domain of skin color classification. This examination was meticulously structured around key performance indicators including accuracy, precision, recall, and the F1-score, with the objective of delineating the comparative merits of each model in aligning classifications with ground truth data. The results derived from this comparison underscored a notable proficiency of the AIDA system, employing the K-means clustering algorithm combined with a matching technique, in the classification of skin colors. An accuracy metric of 0.56 was recorded for AIDA, indicating a successful classification of more than half of the skin color samples in concordance with the ground truth. This level of accuracy signifies a commendable predictive capability inherent within the AIDA model. Precision for AIDA was 0.54, revealing a reasonable efficacy of the model in generating true positive classifications amidst its predictions. Further, a recall rate of 0.54 was observed, suggesting that the AIDA model was capable of correctly identifying a significant proportion of true positive instances in accordance with the ground truth. The F1-score, a harmonic mean of precision and recall, was determined to be 0.53 for AIDA, indicative of a balanced trade-off between the precision and recall metrics.

Conversely, the CNN model's performance was characterized by a discernibly lower efficacy in skin color classification. An accuracy of 0.32 was documented, suggesting that the model's classifications aligned with the ground truth data in merely 32% of instances. This markedly lower accuracy underscores substantial challenges in the CNN model's classification capabilities. Precision was 0.36, indicating a lessened propensity of the model to accurately predict positive classifications. The recall metric of 0.32 further accentuated the CNN model's diminished sensitivity in identifying true positive instances. Moreover, the F1-score for the CNN, recorded at 0.31, significantly lagged behind that of AIDA, emphasizing pronounced limitations in achieving an optimal balance between precision and recall.

A performance analysis, incorporating a +/−1 tolerance level for the prediction of skin colors, revealed a pronounced distinction between the AIDA and CNN models. A tolerance-based accuracy of 97% was achieved by AIDA, illustrating its substantial consistency and reliability within a margin of error deemed clinically acceptable. In comparison, the CNN model exhibited an 87% accuracy under identical conditions, highlighting AIDA's superior precision in closely matching ground truth values. AIDA's predictions demonstrated a notable concentration around the ideal prediction line, particularly within the +/−1 deviation range. This was in stark contrast to the CNN's predictions, which were characterized by a broader dispersion, as evidenced in both scatter plots and histograms. The enhanced performance observed with a +/−1 tolerance underscores AIDA's robustness in predicting FST colors, affirming its dominance over the CNN model. The analysis elucidates that AIDA excelled in achieving exact match accuracy while also exhibiting superior adaptability and precision within a clinical setting, where tolerances are often indispensable. This distinction accentuates the potential of AIDA to significantly advance the field of dermatological diagnostics, offering a more nuanced and accurate approach to skin color classification that accommodates the inherent variability and complexity of human skin tones.

It should be understood that the examples and embodiments described herein are for illustrative purposes only and that various modifications or changes in light thereof will be suggested to persons skilled in the art and are to be included within the spirit and purview of this application. All patents, patent applications, provisional applications, and publications referred to or cited herein are incorporated by reference in their entirety, including all figures and tables, to the extent they are not inconsistent with the explicit teachings of this specification.

What is claimed is:

1. A system for classification of skin color, the system comprising:
   a processor; and
   a machine-readable medium in operable communication with the processor and having instructions stored thereon that, when executed by the processor, perform the following steps:
   i) receiving first data of at least one image of skin of a subject;
   ii) transforming the at least one image of the skin of the subject from an original color space to a standardized color space to give standardized data;
   iii) using an unsupervised learning model to perform clustering and matching on the standardized data to give clustered data; and
   iv) matching cluster centers from the clustered data to cluster centers of a Fitzpatrick skin type (FST) to classify each image of the skin of the subject into an FST color,
   step iii) comprising resizing images of the standardized data, reshaping the images of the standardized data, and iteratively applying the unsupervised learning model until the clustered data is obtained, and
   step iv) comprising calculating color distances, between the cluster centers from the clustered data and the cluster centers of the FST, using a colorimetry metric, followed by matching each cluster centered from the clustered data with a nearest cluster center of the FST based on the calculated color distances.

2. The system according to claim 1, the standardized color space being LAB color space.

3. The system according to claim 1, the subject being a human subject.

4. The system according to claim 1, the system further comprising a display in operable communication with at least one of the processor and the machine-readable medium, and
   the instructions when executed further comprising:
   v) generating a visualization of colors from the at least one image of the skin of the subject with corresponding respective FST colors; and
   vi) displaying the visualization on the display.

5. The system according to claim 1, the system further comprising a ground truth device configured for ground truth classification of the at least one image of the skin of the subject, and
   the instructions when executed further comprising:
   vii) providing the classification of each image to a clinician to compare to ground truth classifications of each image obtained from the ground truth device.

6. The system according to claim 1, the unsupervised learning model being K-means, K-means-PCA, K-means mini-batch, DBSCAN, HDBSCAN, OPTICS, a hierarchical model, a Gaussian mixture model, fuzzy C-means, affinity propagation, mean shift, or spectral clustering.

7. The system according to claim 1, the unsupervised learning model being K-means.

8. The system according to claim 1, the instructions when executed further comprising:
   viii) providing the classification of each image to a clinician to use in diagnosis of a medical condition of the subject.

9. The system according to claim 8, the medical condition being at least one of diabetes and a diabetic foot ulcer.

10. A method for classification of skin color, the method comprising:

i) receiving first data of at least one image of skin of a subject;

ii) transforming the at least one image of the skin of the subject from an original color space to a standardized color space to give standardized data;

iii) using an unsupervised learning model to perform clustering and matching on the standardized data to give clustered data; and iv) matching cluster centers from the clustered data to cluster centers of a Fitzpatrick skin type (FST) to classify each image of the skin of the subject into an FST color, step iii) comprising resizing images of the standardized data, reshaping the images of the standardized data, and iteratively applying the unsupervised learning model until the clustered data is obtained, and step iv) comprising calculating color distances, between the cluster centers from the clustered data and the cluster centers of the FST, using a colorimetry metric, followed by matching each cluster center from the clustered data with a nearest cluster center of the FST based on the calculated color distances.

11. The method according to claim 10, the standardized color space being LAB color space.

12. The method according to claim 10, the subject being a human subject.

13. The method according to claim 10, further comprising:

v) generating a visualization of colors from the at least one image of the skin of the subject with corresponding respective FST colors; and vi) displaying the visualization on a display.

14. The method according to claim 10, further comprising:

vii) providing the classification of each image to a clinician to compare to ground truth classifications of each image obtained from a ground truth device.

15. The method according to claim 10, the unsupervised learning model being K-means, K-means-PCA, K-means mini-batch, DBSCAN, HDBSCAN, OPTICS, a hierarchical model, a Gaussian mixture model, fuzzy C-means, affinity propagation, mean shift, or spectral clustering.

16. The method according to claim 10, the unsupervised learning model being K-means.

17. The method according to claim 10, further comprising:

viii) using the classification of each image to use in diagnosis of a medical condition of the subject.

18. The method according to claim 17, the medical condition being at least one of diabetes and a diabetic foot ulcer.

19. A system for classification of skin color, the system comprising:

a processor;

a display in operable communication with the processor; and a machine-readable medium in operable communication with the processor and having instructions stored thereon that, when executed by the processor, perform the following steps:

i) receiving first data of at least one image of skin of a subject;

ii) transforming the at least one image of the skin of the subject from an original color space to a standardized color space to give standardized data;

iii) using an unsupervised learning model to perform clustering and matching on the standardized data to give clustered data;

iv) matching cluster centers from the clustered data to cluster centers of a Fitzpatrick skin type (FST) to classify each image of the skin of the subject into an FST color;

v) generating a visualization of colors from the at least one image of the skin of the subject with corresponding respective FST colors;

vi) displaying the visualization on the display; and vii) providing the classification of each image to a clinician to compare to ground truth classifications of each image obtained from a ground truth device, the standardized color space being LAB color space, the subject being a human subject, the unsupervised learning model being K-means, step iii) comprising resizing images of the standardized data, reshaping the images of the standardized data, and iteratively applying the unsupervised learning model until the clustered data is obtained, and step iv) comprising calculating color distances, between the cluster centers from the clustered data and the cluster centers of the FST, using a colorimetry metric, followed by matching each cluster center from the clustered data with a nearest cluster center of the FST based on the calculated color distances.

20. The system according to claim 19, the instructions when executed further comprising:

viii) providing the classification of each image to the clinician to use in diagnosis of a medical condition of the subject.

\* \* \* \* \*